(12) United States Patent
Ingram-Campbell

(10) Patent No.: US 11,638,577 B2
(45) Date of Patent: May 2, 2023

(54) UNDERWEAR-INTEGRATED URINE SPECIMEN COLLECTION SYSTEM AND METHOD THEREOF

(76) Inventor: Sybil Ingram-Campbell, Stone Mountain, AR (US)

(*) Notice: Subject to any disclaimer, the term of this patent is extended or adjusted under 35 U.S.C. 154(b) by 243 days.

(21) Appl. No.: 11/632,251

(22) PCT Filed: Jul. 15, 2005

(86) PCT No.: PCT/US2005/025222
§ 371 (c)(1),
(2), (4) Date: Jan. 11, 2007

(87) PCT Pub. No.: WO2006/020074
PCT Pub. Date: Feb. 23, 2006

(65) Prior Publication Data
US 2008/0051742 A1 Feb. 28, 2008

Related U.S. Application Data

(60) Provisional application No. 60/588,592, filed on Jul. 16, 2004.

(51) Int. Cl.
| | |
|---|---|
| *A61M 5/32* | (2006.01) |
| *A61B 10/00* | (2006.01) |
| *A61M 27/00* | (2006.01) |
| *A61F 5/44* | (2006.01) |
| *B65D 83/10* | (2006.01) |
| *B65D 81/02* | (2006.01) |

(52) U.S. Cl.
CPC .................. *A61B 10/007* (2013.01)

(58) Field of Classification Search
CPC ........... A61M 5/32; A61M 27/00; A61F 5/44; B65D 83/10; B65D 81/02; A61B 10/007; A61B 10/358
USPC .... 604/329, 385.1, 369, 386, 389–391, 393, 604/394, 396, 358
See application file for complete search history.

(56) References Cited

U.S. PATENT DOCUMENTS

| | | | | |
|---|---|---|---|---|
| 4,637,061 | A | * | 1/1987 | Riese ............................... 383/38 |
| 4,722,732 | A | * | 2/1988 | Martin .......................... 604/132 |
| 4,797,256 | A | * | 1/1989 | Watlington, IV ............... 422/58 |
| 5,902,297 | A | * | 5/1999 | Sauer ....................... 604/385.19 |
| 6,613,027 | B2 | * | 9/2003 | Kulikov ........................ 604/353 |

FOREIGN PATENT DOCUMENTS

AU 199927688 B2 * 3/1998

* cited by examiner

*Primary Examiner* — Tatyana Zalukaeva
*Assistant Examiner* — Ilya Y Treyger
(74) *Attorney, Agent, or Firm* — Jason P. Webb; Pearson Butler

(57) ABSTRACT

A device and method for facilitating the collection of urine from incontinent or otherwise impaired individuals via an underwear-integrated urine specimen collection system and method thereof, wherein strategically placed semi-permeable tubing collects and retains urine from the underwear substrate and holds the urine for subsequent transfer and testing, wherein a tube-puncturing delivery member is protectively provided to facilitate the transfer of the collected urine to a sealed urine vacutainer, and wherein a microporous filter is incorporated to prevent the transfer of potential contaminants or otherwise undesirable particles into the testing specimen.

6 Claims, 5 Drawing Sheets

UNDERWEAR-INTEGRATED URINE SPECIMEN COLLECTION SYSTEM AND METHOD THEREOF

CROSS-REFERENCE TO RELATED APPLICATION

To the full extent permitted by law, the present Patent Cooperation Treaty Application claims priority to and the benefit of United States Provisional patent application entitled "Integrated Urine Specimen Collection System into Incontinence Disposable Underwear," filed on Jul. 16, 2004, having assigned Ser. No. 60/588,592.

FIELD OF THE INVENTION

The present invention relates generally to urine sample collection systems and, more specifically, to a urine sample collection system that is integrated into disposable underwear, wherein strategically placed semi-permeable tubing collects and retains urine from the underwear substrate for subsequent testing.

BACKGROUND OF THE INVENTION

There is no question that the baby boomer generation is aging. Healthcare, housing, and retirement concerns are becoming priorities. Long term care, assisted living, and rehabilitation facility availability has increased in an effort to support the growing market and the anticipated future onslaught. Moreover, as the senior parents of these boomers have aged, many have required care. Thus, many aging baby boomers have experienced firsthand the helpless heartache, the sad acceptance of a complete shift in the parent child relationship, and the endless pressures and difficulties in caring for an elderly and/or sickly individual.

Today's longer life spans can be attributed to a variety of factors, including the availability of good nutrition and healthcare. Unfortunately, during the later years, the human body often begins to break down. Alzheimer's, osteoporosis, cancer, heart disease, and diabetes each claim an incredible number of lives each year. Those seniors living with or fighting any such affliction often require round-the-clock care. Such care often necessitates frequent monitoring of certain body conditions.

For example, frequent, even daily, urinalysis is necessary for many patients, both inpatient and homebound. Unfortunately, because incontinence also often afflicts the elderly, samples are largely unable to be collected upon demand. Oftentimes, this can result in a need for invasive collection techniques.

Therefore, it is readily apparent that there is a need for a device and method for facilitating the collection of urine from incontinent or otherwise impaired individuals who are unable to provide a urine sample on demand, whereby semi-permeable tubing is incorporated into underwear, thereby enabling urine to be collected without invasive procedures, thus preventing the above-discussed disadvantages.

BRIEF SUMMARY OF THE INVENTION

Briefly described, in the preferred embodiment, the present invention overcomes the above-mentioned disadvantages and meets the recognized need for such a device and method for facilitating the collection of urine from incontinent or otherwise impaired individuals by providing an underwear-integrated urine specimen collection system and method thereof, wherein strategically placed semi-permeable tubing collects and retains urine from the underwear substrate and holds the urine for subsequent transfer and testing, wherein a tube-puncturing delivery member is protectively provided to facilitate the transfer of the collected urine to a sealed urine vacutainer, and wherein a microporous filter is incorporated to prevent the transfer of potential contaminants or otherwise undesirable particles into the testing specimen.

According to its major aspects and broadly stated, the present invention is a device and method for collecting and storing urine, wherein the patient simply wears disposable underwear with the collection materials integrated therein, and urine is automatically collected, when present. Thereafter, the caregiver is able to quickly and easily remove the underwear and transfer the urine to a sterile urine collection tube for testing.

More specifically, the present invention is a urine specimen collection system, wherein, in the preferred form, a disposable incontinence garment is adapted for the passive collection of a sterile urine sample, whereafter, the disposable incontinence garment may be torn away from the body of the wearer for transfer of the collected sample. Tubing is securely incorporated proximate the exterior edges of the crotch area of the underwear, resulting in a collection area defined by the upper, inner legs of the wearer, proximate the genital region. The tubing is formed from semi-permeable, selective membrane to facilitate osmotic flow therein, wherein urine from the wearer is absorbed into the underwear crotch area, and subsequently passed, or wicked, through the pores defined in the membrane surface, into the interior chamber of the tubing. The ability of the tubing to collect sample along its length enables the use of comfortable and non-irritating small-bore tubing, while still facilitating collection of an appropriately sizable sample.

In order to ensure the purity of the collected sample, a micropore filter is provided at the distal end of each tubing member. The micropore filter is intended to facilitate passage of those materials of interest for testing, such as, red blood cells, white blood cells, epithelial cells, casts, crystals, and bacteria, while inhibiting passage of undesirable contaminants if inefficiently excluded by the selective, semi-permeable membrane of the collection tubing. This preferred arrangement positions the distal end of the tubing and the micropore filter proximate the rear portion of the disposable undergarment. Extending from the filter, a collector is defined, wherein the collector is shaped to facilitate the piercing of a vacutainer top for transfer of sample thereto. It is intended that the collector be protectively sheathed to prohibit any undesirable contact of the sharp, pointed end with the wearer.

The underwear-integrated urine specimen collection system may also include a suitable vacutainer-type vial, also built-in to the underwear. For instance, a sealed, yellow-topped urine collection vial may be removably mounted in a padded area proximate the upper rear area of the underwear, in a cross-wise fashion. Such placement would minimize potential discomfort to the wearer, wherein the vial would extend, below and generally parallel to the rear waistline of the wearer.

Additionally, occult blood testing materials could be defined within the disposable incontinence garment, wherein a stool sample could be passively collected and accessed via a perforated flap on the outer underwear surface for subsequent testing. A control area may be included to confirm proper test performance, and test development fluids could be included, on-board, via blister pops, or other suitable means.

It is further envisioned that each of the embodiments may be included in a larger kit grouping, having such other related materials as disposable gloves, vacutainer tubes, transport bags, labels for transport bags, marker for labels, and a waste disposable bag, in addition to the integrated disposable underwear. Further, personal hygiene wipes or any other desirable components may be included in the kit.

A feature and advantage of the present invention is its ability to provide disposable incontinence undergarments that are multi-functional; that is, the present invention introduces a new functional dimension to the disposable underwear.

Another feature and advantage of the present invention is its ability to facilitate the collection of a sterile urine sample from persons who are incontinent.

Another feature and advantage of the present invention is its ability to provide an easy means for urine sample collection that is suitable for use in ambulatory surgery centers, hospitals, physicians offices, nursing homes, and assisted living facilities, as well as in the home.

Another feature and advantage of the present invention is its ability to be utilized when traveling.

Still another feature and advantage of the present invention is its ability to facilitate the collection of urine without necessitating invasive collection techniques.

Yet another feature and advantage of the present invention is its ability to provide a urine collection system that is economical and simple to manufacture.

These and other objects, features and advantages of the invention will become more apparent to one skilled in the art from the following description and claims when read in light of the accompanying drawings.

BRIEF DESCRIPTION OF THE DRAWINGS

The present invention will be better understood by reading the Detailed Description of the Preferred and Alternate Embodiments with reference to the accompanying drawing figures, in which like reference numerals denote similar structure and refer to like elements throughout, and in which.

DETAILED DESCRIPTION OF THE PREFERRED AND ALTERNATE EMBODIMENTS

To the full extent permitted by law, the present Patent Cooperation Treaty Application claims priority to and the benefit of United States Provisional patent application entitled "Integrated Urine Specimen Collection System into Incontinence Disposable Underwear," filed on Jul. 16, 2004, having assigned Ser. No. 60/588,592.

In describing the preferred and alternate embodiments of the present invention, as illustrated in the figures and/or described herein, specific terminology is employed for the sake of clarity. The invention, however, is not intended to be limited to the specific terminology so selected, and it is to be understood that each specific element includes all technical equivalents that operate in a similar manner to accomplish similar functions.

Figure 1:
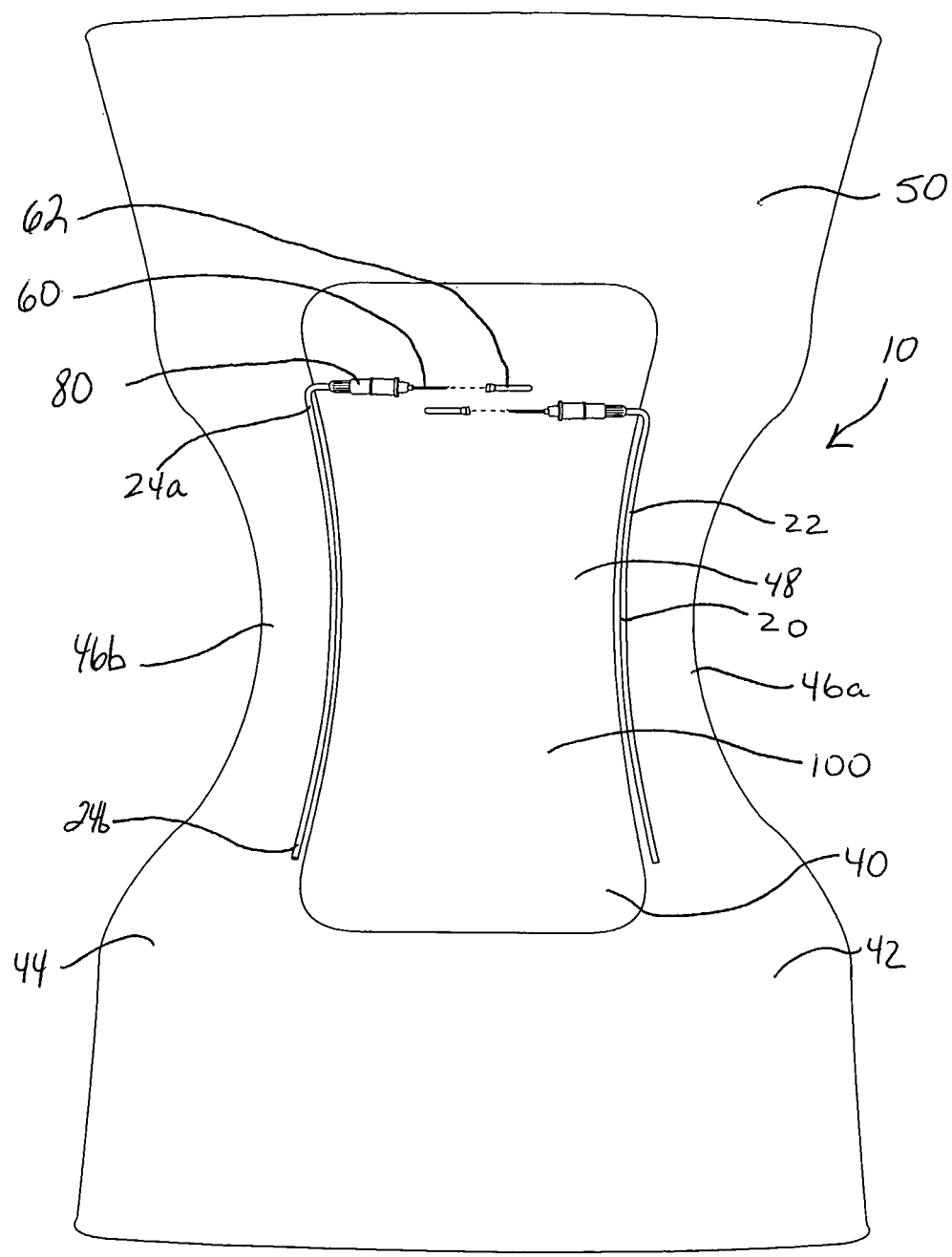
FIG. 1 is an overhead view of an underwear-integrated urine specimen collection system according to the preferred embodiment of the present invention, showing the underwear in a fully opened position, with sides disconnected.

Referring now to FIG. 1, the present invention in its preferred form is underwear-integrated urine specimen collection system 10 and method thereof, wherein semi-permeable tubing 20 preferably, passive to the wearer, collects and retains urine from underwear substrate 40 and holds the urine for subsequent transfer and testing, wherein tube-puncturing delivery member 60 is preferably provided to facilitate the transfer of the collected urine for subsequent testing, and wherein microporous filter 80 is preferably incorporated to prevent the transfer of potential contaminants or otherwise undesirable particles into the testing specimen.

It is important to understand that the present invention is suitable for utilization with any type incontinence undergarment 42, such as, for exemplary purposes only, disposable or reusable, having an integrally formed panty or a diaper-style configuration, and/or having an inner liner or pad configuration or an integral collection substrate; therefore, while the device of the present invention is described conveniently in the preferred utilization within a disposable panty-style undergarment with an integral collection substrate, it is not limited to such application or implementation.

Preferably, incontinence garment 42 is disposable, with tear-away construction, and is adapted with semi-permeable tubing 20 securely incorporated proximate exterior edges 46a and 46b of inner crotch area 48, wherein preferred urine collection area 100 is defined, relative to the wearer, in underwear substrate 40, proximate the upper, inner thighs, proximate the genital region. The preferred semi-permeable, selective nature of tubing 20 facilitates the intake of fluid, particularly urine, while simultaneously preventing the passage of undesirable components into the interior of the tube and preventing the egress of the absorbed sample fluid, once inside.

Thus, the affinity of underwear substrate 40 for urine is exploited, wherein the collected urine is preferably wicked and/or passed to and through micropores defined in membrane surface 22 of semi-permeable tubing 20. The tubing 20, as illustrated, includes no open apertures larger than the micropores. The tubing 20, being a tube, defines a cavity inside thereof. That is, preferred tubing 20 osmotically collects urine from the wearer via the underwear substrate 40 within urine collection area 100. In the preferred embodiment, semi-permeable tubing 20 is adapted for urine intake along its length, thereby maximizing sample collection volume while minimizing tubing bore requirements.

Micropore filter 80 is preferably incorporated proximate distal end 24a of tubing 20, whereby purity of the collected sample is further ensured. Preferably, micropore filter 80 is adapted to facilitate passage of those materials traditionally of interest for testing, such as, red blood cells, white blood cells, epithelial cells, casts, crystals, bacteria, and/or any other materials of interest, while inhibiting passage of undesirable contaminants. Thus, micropore filter 80 preferably provides a second-level of selective filtration, following that first-level of selective filtration provided by the selective, semi-permeable membrane surface 22 of collection tubing 20.

The preferred arrangement of tubing 20 positions distal end 24a of tubing 20, along with micropore filter 80, proximate rear portion 50 of incontinence undergarment 42. Although this arrangement for tubing 20 and micropore filter 80 is preferred, one skilled in the art will readily recognize that micropore filter 80 could be positioned proximate end 24b of tubing 20. Further, tubing 20 could be alternately configured and/or positioned within urine collection area 100 of incontinence undergarment, wherein greater or lesser lengths of tubing 20 could be incorporated, one or more lengths of tubing 20 could be utilized, and the possible arrangements of tubing 20 relative to urine collection area 100 could be essentially infinite.

Preferably, tube-puncturing delivery member 60 is positioned proximate filter 80, wherein tube-puncturing delivery member 60 is preferably shaped to facilitate the piercing of a vacutainer cap for transfer of sample thereto. Also preferably, tube-puncturing delivery member 60 is protectively sheathed by removable cover 62, thereby prohibiting undesirable sharp contact with the wearer. It is envisioned that underwear-integrated urine specimen collection system 10 could be configured without the integral inclusion of tube-puncturing delivery member 60, wherein any similar or equivalent fluid transfer device could be installed subsequent to removal of undergarment 42 from the wearer. Similarly, microporous filter 80 could be installed subsequent to removal of undergarment 42 from the wearer, in lieu of integral inclusion.

In the preferred use, an individual simply wears incontinence undergarment 42 with integrated urine specimen collection system 10 and urine is automatically collected by tubing 20, when present. Thereafter, a caregiver preferably removes undergarment 42, preferably by tearing the disposable sides, thereby enabling easy access to tubing 20, wherein the collected urine is subsequently transferred to a collection tube 110 for testing.

Figure 2:
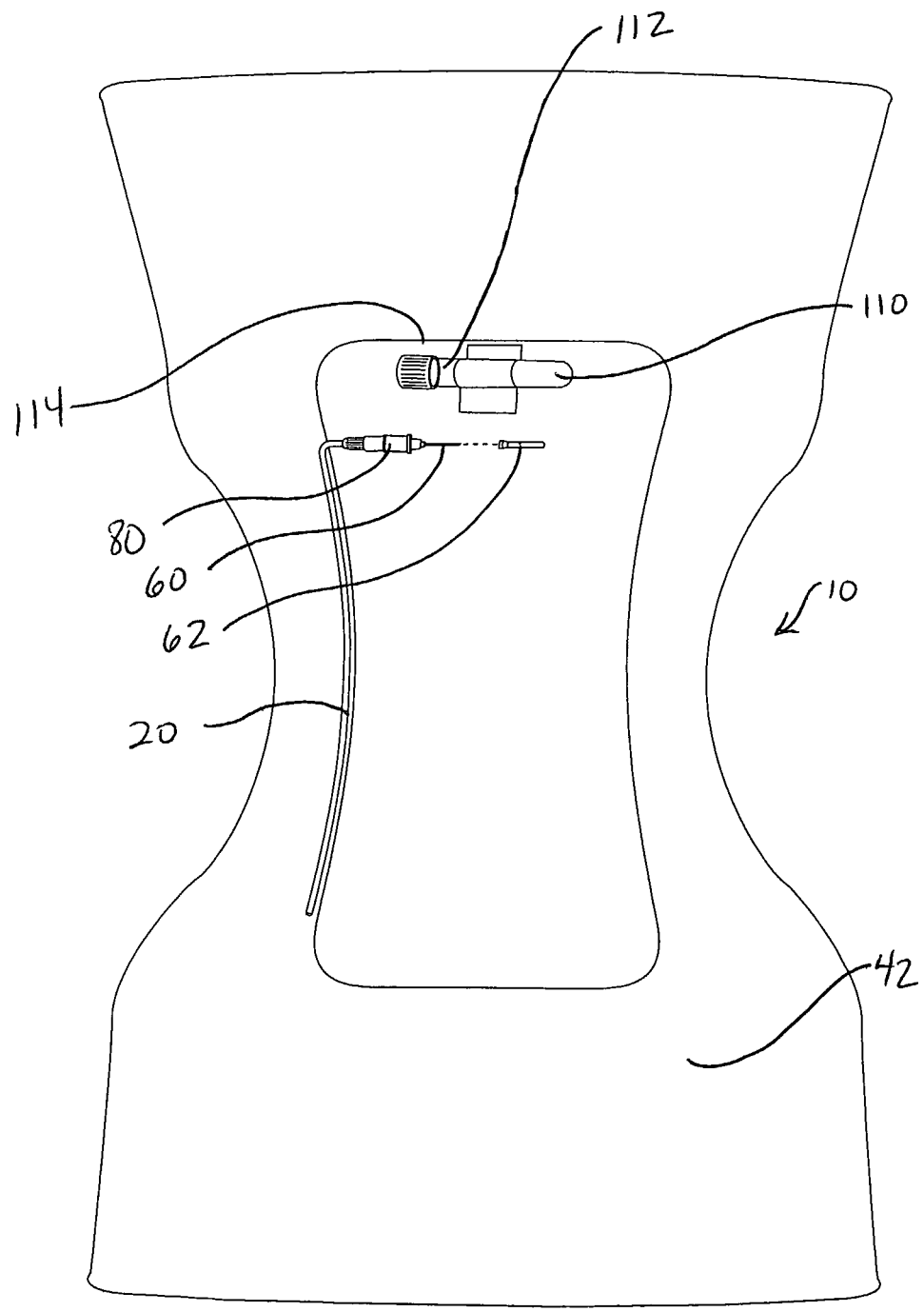
FIG. 2 is an overhead view of an underwear-integrated urine specimen collection system according to an alternate embodiment of the present invention, showing the underwear in a fully opened position, with sides disconnected and an on-board vial.

Referring now to FIG. 2, in an alternate embodiment, underwear-integrated urine specimen collection system 10 could further include collection vial 110, wherein vial 110 could be yellow-capped urine collection vacutainer 112, or any other suitable type of collection vial. Collection vial 110 could be removably mounted in padded area 114 proximate rear portion 50 of incontinence undergarment 42, in a cross-wise fashion. Such placement would minimize potential discomfort to the wearer, wherein collection vial 110 would extend, below and generally parallel to the rear waistline of the wearer. Other placement arrangements could also be utilized, and/or more than one collection vial 110 could be included.

Figure 3:
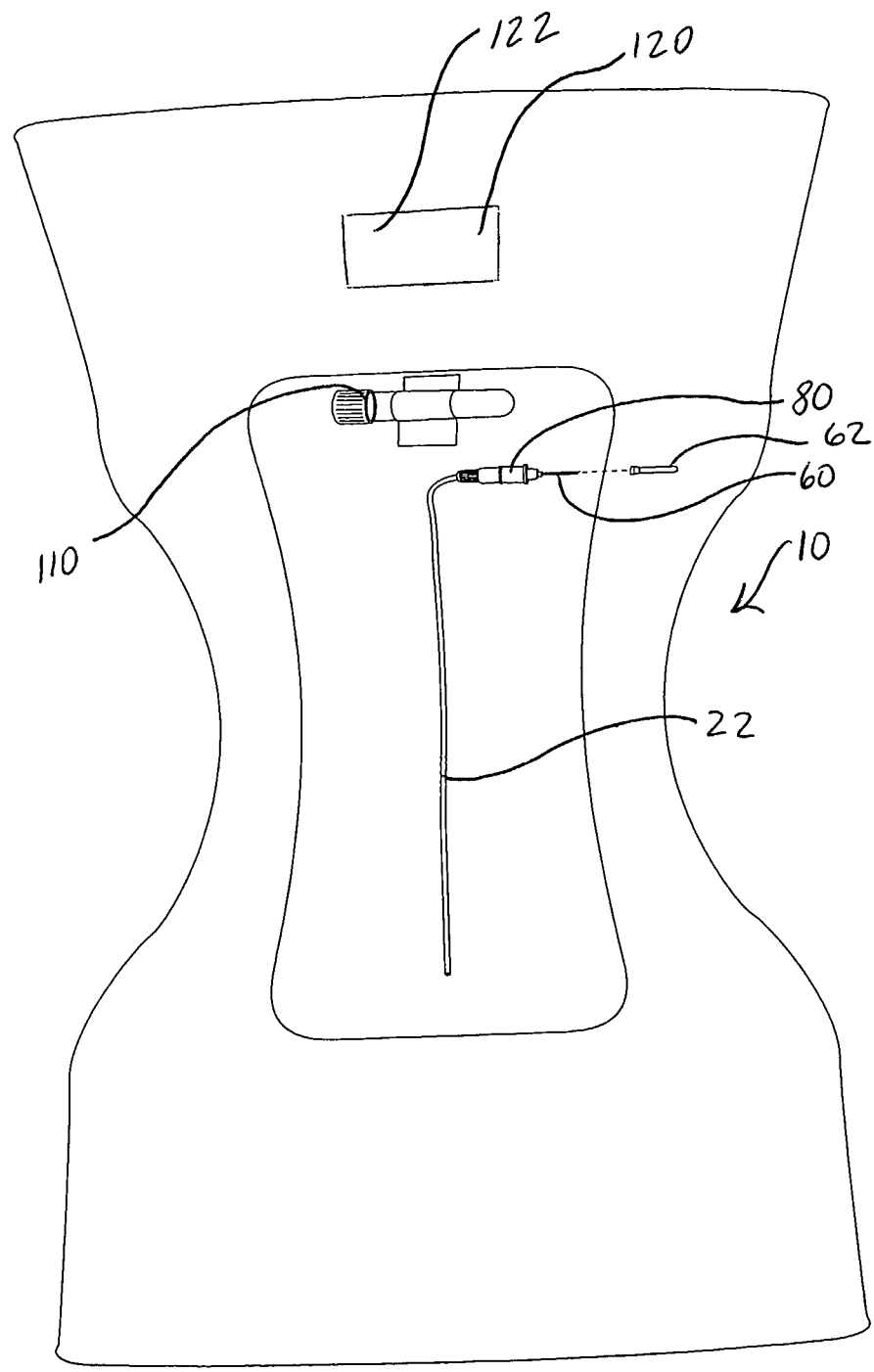
FIG. 3 is an overhead view of an underwear-integrated urine specimen collection system according to an alternate embodiment of the present invention, showing the underwear in a fully opened position, with sides disconnected, alternately positioned tubing, and an occult blood test collection area.
Figure 4:
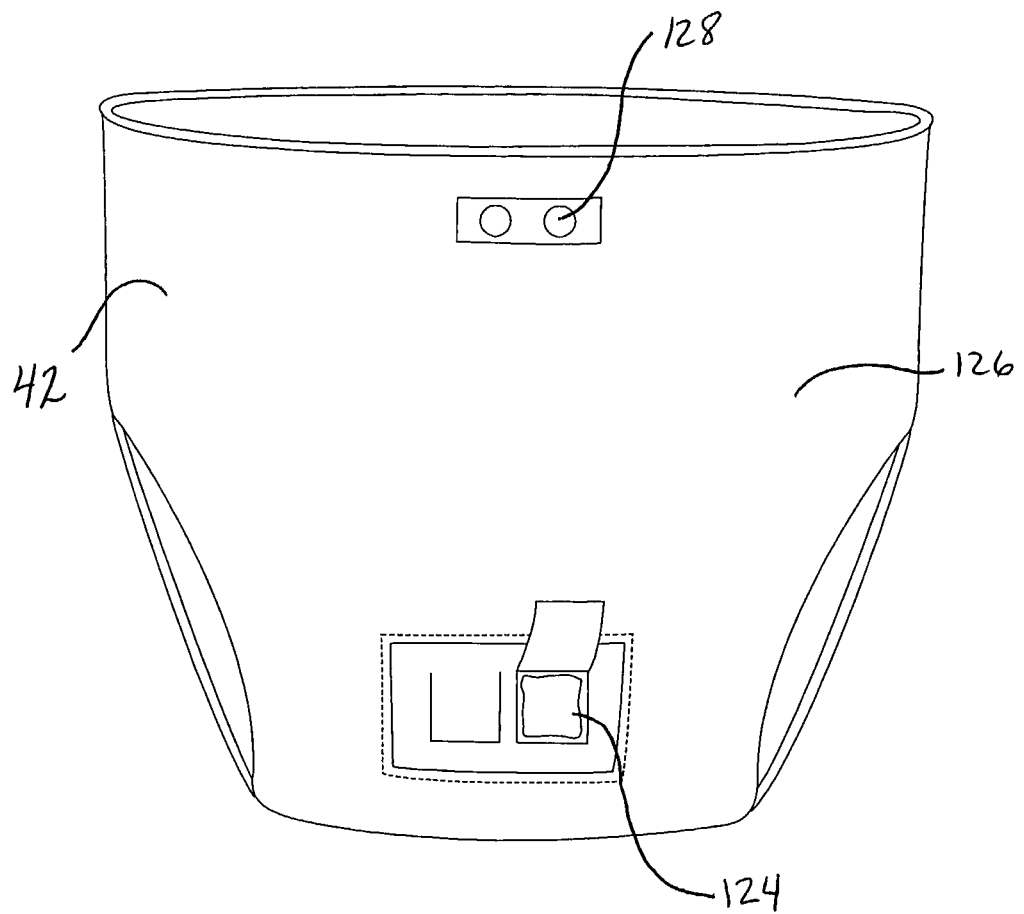
FIG. 4 is a rear view of an underwear-integrated urine specimen collection system according to an alternate embodiment of the present invention, showing an occult blood testing area.

In another alternate embodiment, semi-permeable tubing 20 could be positioned away from exterior edges 46a and 46b of inner crotch area 48, such as in a generally centralized position, as depicted in FIG. 3, or in any other type configuration or direction, with one or more tubing 20 members provided in virtually any arrangement that would enable sample collection from urine collection area 100 while remaining comfortable and non-irritating during wear.

Additionally, occult blood testing materials 120 could be defined within incontinence undergarment 42, wherein a stool sample could be passively collected from the wearer, with transfer to occult test collection surfaces 122 for subsequent testing, wherein such surfaces can comprise guaiac impregnated paper or similar appropriate testing components. Test access could be provided via perforated flaps 124 on outer rear surface 126 of undergarment 42. A control area could also be included to confirm proper test performance and/or such control could be separately provided with additional test materials, such as development fluids. Further, occult test development fluids, such as a developing solution of denatured ethyl alcohol and hydrogen peroxide, could be included, on-board undergarment 42, via blister pops 128, or other suitable development fluid carrier.

Figure 5:
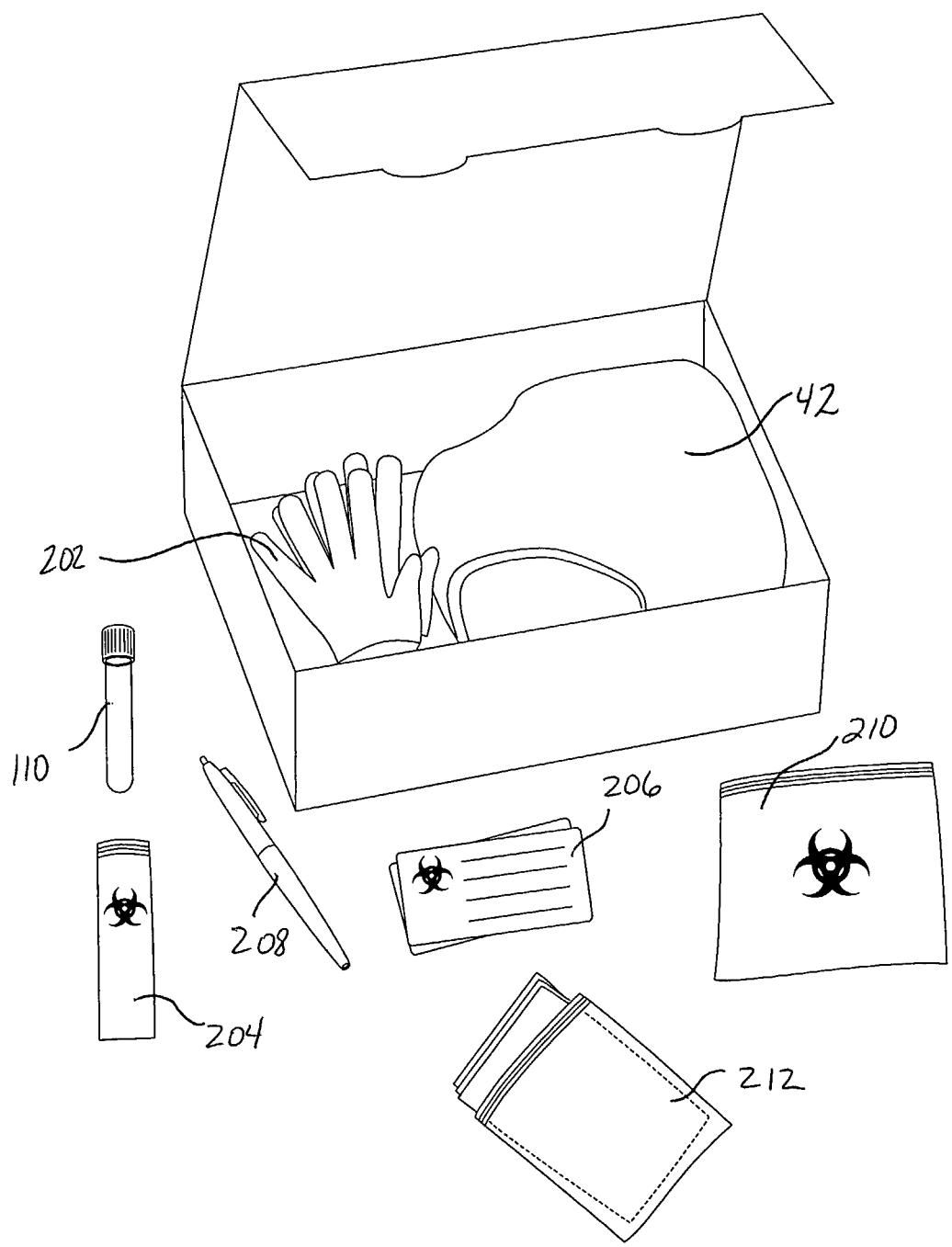
FIG. 5 is a perspective view of an underwear-integrated urine specimen collection system according to an alternate embodiment of the present invention, showing selectable kit components.

It is further envisioned that underwear-integrated urine specimen collection system 10 could include kit 200, wherein a variety of selectable materials could be provided therein. For example, referring to FIG. 5, related materials could include disposable gloves 202, collection vials 110, sample transport bags 204, labels 206, marker 208, and/or waste disposal bags 210, in addition to disposable undergarment(s) 42. Further, personal hygiene wipes 212, urine collection straw (not shown) and/or any other desirable components or combination thereof may be included in kit 200.

Having thus described exemplary embodiments of the present invention, it should be noted by those skilled in the art that the within disclosures are exemplary only, and that various other alternatives, adaptations, and modifications may be made within the scope of the present invention. Accordingly, the present invention is not limited to the specific embodiments illustrated herein, but is limited only by the following claims.

I claim:

1. An underwear-integrated urine specimen collection system, comprising:
   an undergarment; and
   semi-permeable tubing for osmotically collecting urine from the wearer, said semi-permeable tubing is carried by said undergarment and comprises micropores, said semi-permeable tubing is sealed at its proximal end, said semi-permeable tubing not including any open apertures other than the micropores, the semi-permeable tubing adapted to absorb and contain at least some components of urine within a cavity defined by the tubing, said collection system further comprising a microporous filter disposed and the distal end of the semipermeable tubing and a tube puncturing delivery member proximate said microporous filter, said tube puncturing delivery member is disposed at the proximal side of the semi-permeable tubing and shaped to facilitate the piercing of a vacutainer cup to transfer the sample thereto.

2. The underwear-integrated urine specimen collection system of claim 1, further comprising a vacutainer carried by said undergarment.

3. The underwear-integrated urine specimen collection system of claim 1, further comprising occult blood testing surfaces defined in said undergarment.

4. The underwear-integrated urine specimen collection system of claim 3, further comprising occult test development fluid carried within a fluid carrier supported by said undergarment.

5. The underwear-integrated urine specimen collection system of claim 1, further comprising a kit, said kit comprising materials selected from the group of disposable gloves, collection vials, sample transport bags, labels, marker, waste disposable bags, and personal hygiene wipes.

6. A method of urine-specimen collection comprising the steps of:
- a) obtaining an underwear-integrated urine specimen collection system comprising semi-permeable tubing for osmotically collecting urine from the wearer, said semi-permeable tubing is carried by said undergarment and comprises micropores, said semi-permeable tubing is sealed at its proximal end, said semi-permeable tubing not including any open apertures other than the micropores, the semi-permeable tubing adapted to absorb and contain at least some components of urine within a cavity defined by the tubing, said collection system further comprising a microporous filter disposed and the distal end of the semipermeable tubing and a tube puncturing delivery member proximate said microporous filter, said tube puncturing delivery member is disposed at the proximal side of the semi-permeable tubing and shaped to facilitate the piercing of a vacutainer cup to transfer the sample thereto;
- b) placing said undergarment on a wearer;
- c) removing said undergarment from the wearer subsequent to urination; and
- d) transferring urine from said collection tubing to a collection vessel.

\* \* \* \* \*